(12) United States Patent
Blundell

(10) Patent No.: US 8,524,255 B2
(45) Date of Patent: Sep. 3, 2013

(54) LINGUAL VESTIBULAR DOSAGE-FORM AND DELIVERY SYSTEM FOR TRANSMUCOSAL ADMINISTRATION OF PHARMACEUTICAL AGENTS

(75) Inventor: Garrett Douglas Blundell, College Station, TX (US)

(73) Assignee: noesisBIO LLC, College Station, TX (US)

( * ) Notice: Subject to any disclaimer, the term of this patent is extended or adjusted under 35 U.S.C. 154(b) by 0 days.

(21) Appl. No.: 13/252,027

(22) Filed: Oct. 3, 2011

(65) Prior Publication Data
US 2013/0084311 A1    Apr. 4, 2013

(51) Int. Cl.
*A01N 25/34* (2006.01)
*A61F 13/00* (2006.01)

(52) U.S. Cl.
USPC ............. 424/400; 424/404; 424/402; 604/20

(58) Field of Classification Search
USPC ....................................................... 424/400
See application file for complete search history.

(56) References Cited

U.S. PATENT DOCUMENTS

| | | | | |
|---|---|---|---|---|
| 4,820,525 | A * | 4/1989 | Leonard et al. | 424/486 |
| 6,319,510 | B1 * | 11/2001 | Yates | 424/404 |
| 7,645,137 | B2 * | 1/2010 | Wasyluch | 433/29 |
| 7,967,145 | B2 * | 6/2011 | Tchouangang | 206/570 |
| 2010/0286587 | A1 * | 11/2010 | Gross | 604/20 |
| 2011/0027746 | A1 * | 2/2011 | McDonough et al. | 433/80 |

OTHER PUBLICATIONS

Perioli et al.; "Development of mucoadhesive patches for buccal administration of iBuprofen"; Journal of Controlled Release 99 (2004), p. 74-82; publised by Elsevier.*
"The coma cocktail: indications, contraindications, adverse effects, proper dose, and proper route" by Bartlett et al; From Journal of emergency nursing, (2004), 30(6), 572-4; Database: Medline.*
Perioli et al.; "Development of mucoadhesive patches for buccal administration of ibuprofen"; J. Controlle release; 99, p. 74-82, 2004; published by Elsevier. Mailed in previous office action.*
Bartlett et al.; "Thecoma cocktail: indications, constraindications, adverse effects, proper dose, and proper route"; J. of Emergency nursing, (2004), 30(6), 572-4; published by MEDLINE. Mailed in previous office action.*

* cited by examiner

*Primary Examiner* — Janet Epps-Smith
*Assistant Examiner* — Yanzhi Zhang
(74) *Attorney, Agent, or Firm* — Matthew J. Esserman

(57) ABSTRACT

A pharmaceutical delivery system enabling the oral transmucosal administration of active pharmaceutical agents in a situation where rapid transmucosal administration is preferred to prevent the delay and decomposition of the agents in passing through the intestinal tract. The delivery system comprises a supportive substrate with bilateral lingual vestibular flanges connected at the anterior midline to form a 'U' like shape for fitting in the potential space of the bilateral lingual vestibules, and further comprising a handle or tab for holding the device in the mouth of a patient with altered consciousness to prevent aspiration or premature swallowing. The pharmaceutical dosage-form is formulated and shaped to contact the mucosal tissues and may include mucoadhesive compounds, retentive compounds, and/or additional payload enhancers, such as permeation enhancers and flavor enhancers.

26 Claims, 3 Drawing Sheets

LINGUAL VESTIBULAR DOSAGE-FORM AND DELIVERY SYSTEM FOR TRANSMUCOSAL ADMINISTRATION OF PHARMACEUTICAL AGENTS

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

Millions of surgeries are performed each year under local anesthesia and/or intravenous (IV) sedation in freestanding ambulatory surgery centers. In any procedure, the patient is often faced with significant distress and anxiety which can lead to many problems. In addition to the physiologic changes caused by anxiety and pre-procedural stress, the patient's ability to follow pre-op instructions is often compromised. This can be of a particular problem in patients such as diabetics who are often confused about which medicines and how much of each they should or should not take in the pre-op period. This, coupled with the fact that patients often need to refrain from eating or drinking (nothing by mouth or Latin: Nil Per Os or NPO) for an extended period of time prior to the procedure, can lead to problems such as significant and symptomatic hypoglycemic episodes.

Minor medical emergencies in a non-hospital, office-based environment can pose challenges. Often, in the stable and fully conscious patient with mild hypoglycemia, a glucose-rich Per Os (by mouth, Latin: Per Os or PO) drink is administered. Such intervention is practical in these mildly affected patients where a more acute intervention is not necessary.

In a more acute situation where quick reversal of hypoglycemia is required, dextrose may be administered via IV access. However, the option of IV administration would take some time to prepare and push even in the event that an IV is already in place. Intervention with IV dextrose alone would likely be slower than optimal or desirable in those patients who do not already have IV access.

Intervention in the form of the application of a sugar-rich substance such as cake icing to the buccal or sublingual mucosa is often advocated and a possible option in the event that an IV is not accessible or if dextrose infusion is not immediately available. This option, in addition to having no data supporting its efficacy, has other problems as well. Application should only be used in a fully conscious and alert patient due to the risk of pulmonary aspiration. There is also a dependence on patient compliance even in the conscious persons. If the sugar is swallowed, there would be a significant delay in the effects on blood glucose levels. Another problem is the delay necessary for the sugar, in the form of sucrose, to be broken down by sucrase in the oral cavity prior to being able to be transported transmucosally as glucose.

If the above treatments are not administered without delay, a patient, particularly those with brittle (labile) diabetes, may become comatose due to hypoglycemic brain injury. In certain situations this can lead to a persistent vegetative state without any expected neurologic improvement. Quick and acutely effective sources of glucose, administered expeditiously during crashing could be the difference between life and death. Of additional importance, the dose of dextrose required to effect a change in the blood glucose of an individual is approximately 5 to 15 grams—necessitating the ability to deliver a large dextrose payload.

The problem and risk of hypoglycemic episodes for the diabetic is not limited to the medical or dental office, however, and constant access to a source of rescue glucose is crucial. It is not uncommon for physicians to recommend that these individuals keep a tube of cake icing or other glucose rich substance on their person for quick application in such events. As enumerated earlier, the use of either cake icing or PO forms of rescue glucose pose significant problems and are suboptimal for these same reasons.

Hypoglycemia of the newborn and hypoglycemia associated with severe systemic illness is a significant health problem worldwide, particularly in the undeveloped world. Hypoglycemia can be closely linked to a significant proportion of the two hundred and twenty-five thousand (225,000) yearly malarial deaths in African children under the age of five (5) years. The preferred treatment in most cases is correction via IV dextrose infusions. Problems with this treatment are plentiful in the undeveloped areas that are poor both in terms of monetary and human capital. Delay to infusion can be caused by many reasons. Most health care facilities do not have the supplies. Families of the sick are given prescriptions for needed supplies/medications and they must go and find not only the money to buy these supplies but a pharmacy that has the supplies available prior to returning to the hospital for initiation of treatment. Additionally, it can be hard to obtain IV access in a small, acutely ill (dehydration, shock, unconscious) child. IV access carries other risks, including pain, risk of blood-borne pathogen transmission, and possible local or systemic infection associated with venous catheterization.

The correction of hypoglycemia by placing a spoon full of granulated table sugar (sucrose) under the tongue has been studied in this population by the medical community and the results were promising when compared to IV dextrose infusion. Problems with this very basic method, however, included early swallowing of the loose, granulated sugar by the children which resulted in treatment failure. Additionally, table sugar is sucrose and must be broken down to glucose and fructose by sucrase in the oral cavity prior to transport transmucosally.

Hypoglycemia is of immediate concern in the person found by healthcare workers to be unconscious due to an unknown cause. Classically, such a patient is always treated, immediately on arrival in the emergency department, with an intravenous administration of a three drug combination including dextrose, thiamine, and naloxone. The decision to administer these drugs is a reflexive decision (i.e. all unconscious patients with a significantly and abnormally depressed mental status, without a clear or known cause for such, are reflexively administered this "coma cocktail.") If such a transmucosal dosage-form were possible, under the reflexive direction of a proper protocol, it would allow for the administration of the classic cocktail constituents by emergency medical services providers immediately upon arrival to the scene and long before IV access or reaching the hospital emergency department.

Long-distance athletes have a need to obtain hydration, electrolytes, and carbohydrates during the episodes of intense and prolonged exertion that they often put themselves through. Many different carbohydrate formulations, predominantly meant to be consumed orally, have been developed to target this population. A popular embodiment involves a gel-type formulation that is stored in a small pouch and meant to be consumed at some time period during the extended physical exertion. Targeting the PO route with these carbohydrate loads have multiple unwanted side effects—all of which have to do with the normal gastrointestinal physiology. Stimulation of the gastrointestinal tract with a load of carbohydrate, causes increased neuronal activity to the area leading to increased peristalsis which combined with the decreased blood supply to the bowels during strenuous exertion produces the common sensation of gastrointestinal uneasiness or queasiness after consuming the product. The next step in physiology is an increased shunting of blood away from the muscles needing this perfusion to the splachnic circulation towards the bowels. Athletes also describe the subjective feeling of a vague central heaviness.

Prior art, with regard to oral, transmucosal drug delivery does not describe a method by which large payloads of active pharmaceutical agent, on the order of grams, can be delivered systemically. The prior art of dosage form fabrication for oral transmucosal drug delivery describes gels, tabs, patches, sprays. It lacks in having not described a form by which large payloads (on the order of multiple grams) can be delivered systemically through the mucosa of the oral cavity. It has also not described anatomic delivery forms for oral application.

DETAILED DESCRIPTION OF THE PREFERRED EMBODIMENTS

Figure 1:
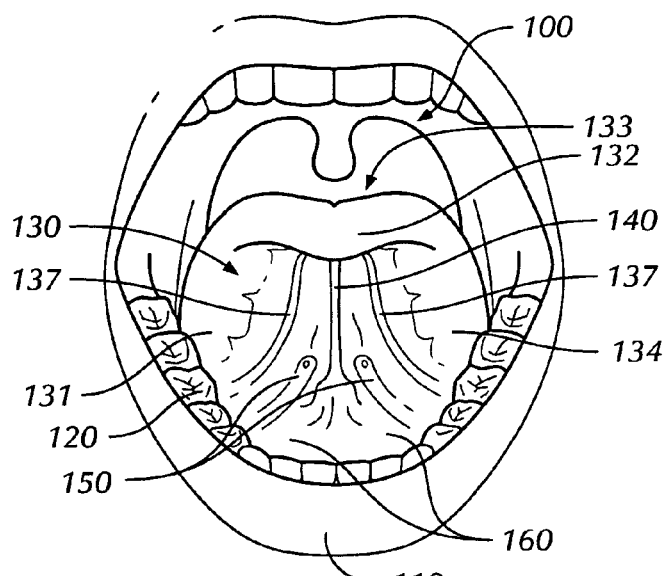
FIG. 1 illustrates the parts of the oral cavity (prior art).

Described herein is a transmucosal dosage-form for delivery to the oral cavity substances in a large payload, on the order of 5+ grams, in order to deliver therapeutic amounts of substances systemically. Substances may be, but are not limited to pharmaceuticals and other active agents. A transmucosal dosage-form for delivery of dextrose, thiamine, and naloxone (i.e. the "coma cocktail"), would allow for immediate administration by a health care worker upon encountering an unconscious patient without the delay of starting an IV. The problem is that there was previously no method of such a transmucosal dosage-form of any one of these drugs, much less all three in a dosage adequate to accommodate the amount of pharmaceutical payload necessary to deliver therapeutic amounts of these drugs systemically. Further, by the description herein, we describe a transmucosal dosage-form for delivery to the oral cavity of agents which may be used for delivery of dextrose for treatment of hypoglycemia without fear of aspiration.

A bilateral lingual vestibular mucoadhesive, transmucosal dosage-form and delivery system for pharmaceutical payload delivery can provide a quick, easy, and safe means of treatment, even in patients whose consciousness is questionable, with the capacity to deliver large pharmaceutical payloads. In one embodiment pharmaceutical payloads of 5 to 10 grams could be delivered by the system. A polymeric mucoadhesive carrier matrix, serving as one possible type of a supportive substrate, binds the pharmaceutical payload to the mucosal tissue in the lingual vestibules to overcome the displacing forces created by salivary flow in the area and combat the risk of treatment failure due to premature patient swallowing or patient aspiration. By using a general or anatomical shape, the dosage-form is also physically secured in the lingual vestibular region by the lingual frenulum and the tongue to hold it against the thin mucosa overlying the dense vasculature of the floor of the mouth and ventral tongue, preventing it from migrating. The retention of the dosage-form can be further enhanced by the addition of a handle, its purpose serving both to aid insertion and allowing for external control of the dosage-form position once placed. The pharmaceutical payload may be an active pharmaceutical agent, a medicament, and/or other active or passive substances.

In one embodiment, there is an embedded supportive substrate to which a pharmaceutical payload is molded or otherwise adhered. In such an embodiment the supportive substrate may be partially or substantially enclosed within the pharmaceutical payload. The pharmaceutical payload may be molded, formed, or otherwise shaped into either a general or a specific anatomical shape to fit the lingual vestibular space. In one embodiment, the shape is anatomical to fit the potential space formed by the bilateral lingual vestibules. In another embodiment the dosage-form payload is formed into a generally cylindrical or rectangular shape which is curved along the center so that the ends are substantially parallel forming a "U" like shape. In another embodiment, the dosage-form is shaped to fit a unilateral lingual vestibular space of either the left or right side. Such a dosage-form could be used alone, in pairs, or in conjunction with another dosage-form containing a different combination of active pharmaceuticals. One skilled in the art would appreciate that other forms could be utilized in accordance with the teachings herein.

In another embodiment the supportive substrate forms the structure of at least a generally anatomical shape designed in a manner to fit into the lingual vestibule. In such an embodiment the supportive substrate may be semi-permeable and impregnated with a pharmaceutical payload. As an alternative, in such an embodiment, the supportive substrate may be coated in a pharmaceutical payload. One skilled in the arts would appreciate other configurations for mating the pharmaceutical payload to the supportive substrate in a manner consistent with an exemplary embodiment of the invention.

A pharmaceutical dosage-form may be comprised of any active pharmaceutical agent which may be administered in a transmucosal manner. Many such pharmaceutical agents benefit from avoidance of the degradation, delay, and/or unpredictability of passing through the gastrointestinal track before finding its way into other of the body systems. Examples of such pharmaceutical agents include, but are not limited to: Dextrose, Thiamine, Naloxone, Alanine, Terbutaline, and Arginine.

A pharmaceutical dosage-form may further be comprised of agents that enhance the transmucosal transportation of an active agent (permeation enhancers). Examples of such permeation enhancers include, but are not limited to: bile salts such as sodium cholate, sodium glycocholate, sodium glycodeoxycholate, taurodeoxycholate, sodium deoxycholate, sodium lithocholate chenocholate, chenodexoycholate, ursocholate, ursodeoxy-cholate, hyodeoxycholate, dehydrocholate, glycochenocholate, taurochenocholate, taurochenodeoxycholate. Others include sodium dodecyl sulfate ("SDS"), dimethyl sulfoxide ("DMSO"), sodium lauryl sulfate, salts and other derivatives of saturated and unsaturated fatty acids, surfactants, bile salt analogs, derivatives of bile salts, capsaicin, histamine, or any other additives which may positively augment the transmucosal absorption of the active pharmaceutical payload. Once skilled in the art would appreciate that different permeation enhancers would be used depending on the active agents used in a particular dosage-form and a particular patient target.

A pharmaceutical dosage-form may further be comprised of components which aid in binding the payload to the mucosal tissue in an effort to avoid migration and maximize transmucosal transportation. These mucoadhesives or mucoretentive polymers or compounds may serve to form the supportive substrate of the dosage-form or may serve as a component of the substance payload itself. Such mucoadhesives may be natural, and/or synthetic in the form of polymers and/or reservoirs with tissue adhesives. Examples include, but are not limited to: chitosan, mucilage, hydrogel, sodium alginate, sodium carboxymethylcellulose, guar gum, xanthum gum, hydroxyethylcellulose, karya gum, methylcellulose, polyethylene glycol (PEG), retene, tragacanth, Poly (acrylic acid), Polycarbophil, carbopol, polyox, chitosan-cysteine, chitosan-thiobutylamidine, chitosan-thioglycolic acid, poly (acrylic acid)-cysteine, poly (acrylic acid)-cysteamine, carboxymethylcellulose-cysteine, alginate-cysteine, polaxamer. In an alternative embodiment, a plurality of active pharmaceutical agents, payload enhancers, and/or flavor enhancers may be combined in the dosage-form to act synergistically. One skilled in the art would appreciate that the composition of the dosage-form may contain various permutations of the above in varying percentages depending on the intended treatment, the targeted patient type, and the specific condition.

The preferred embodiment is a bilaterial lingual vestibular dosage-form and delivery system comprised of an anatomic three-dimensional matrix formed by the combination, in solutions, of a mucoadhesive compound, active substance/agent payload(s), and any additional modifying compounds such as permeation enhancers which is formed to the approximate anatomical shape of the bilateral lingual vestibules. The achievable payload allowed by fabricating a dosage-form and delivery system that targets the bilateral lingual vestibules can be as high as 5-10 grams in an average patient Further, fabricating the dosage-form in an anatomic shape of the lingual vestibule aids in maximizing the mucosal surface area engaged by active pharmaceutical agent thereby optimizing speed and amount of transmucosal payload transportation. The bilateral lingual vestibular delivery system may further comprise a fixed or detachable handle apparatus which could be used to place and secure the device in the oral cavity, specifically the lingual vestibule of a patient experiencing a hypoglycemic episode, particularly in a situation where altered conscious makes normal PO delivery unsafe due to the danger of aspiration; or where timing, lack of equipment, or lack of expertise makes the use of IV delivery unviable; and other methods would not yield delivery of a sufficient sized payload for transmucosal uptake into the systemic circulation.

Through an indirect impression technique, it is possible to model an anatomic negative representation of the bilateral lingual vestibules. This is best achieved through the proper use of an elastomeric impression material, such as a polyvinyl siloxane rubber base. This negative representation of the bilateral lingual vestibules is then used to create the reciprocal positive form which can be accomplished using a material, such as die stone, which has a working state that is fluid and a final, set state that is solid and stable. From this solid positive representation of the bilateral lingual vestibules, a mold, for subsequent dosage-form production, can then be fabricated using a material of choice. With this exact negative mold of the targeted lingual vestibule, an anatomic lingual vestibular dosage-form can be fabricated. In one embodiment, the dosage-form of the delivery system is comprised of an active pharmaceutical agent(s) and permeation enhancer(s) combined within a polymeric, mucoadhesive matrix which is produced in the form of the bilateral lingual vestibules via the fabrication processes enumerated above. Additionally, it is possible to commercialize an anatomically-shaped dosage-form by generalizing the dosage-form size in production so that the dosage-forms are subsequently applied to patients based on the patient's sex and/or size, and/or other physical attributes. Averages of the general anatomic curvatures of the bilateral lingual vestibules, obtained via the above enumerated impression procedures, can guide scaling of the dosage-forms in production to fit differing sized individuals. One skilled in the art would appreciate that such a shape may be approximated by several other methods which would suit the requirements embodied within this disclosure.

Employing an alternative embodiment, athletes having a need to obtain hydration, electrolytes, and carbohydrates during the episodes of intense and prolonged exertion may avoid the gastrointestinal uneasiness, queasiness, and vague central heaviness that accompany normal PO route carbohydrate loads. The ability to transport sufficiently larger payloads of dextrose, for instance, transmucosally in the oral cavity via a mucoadhesive delivery form/device allows for systemic effects without stimulating the unwanted gastrointestinal physiology. The primary payload (ie dextrose) could additionally be accompanied by adjunct constituents to maximize athletic performance (ie alanine, arginine, electrolytes, etc.)

As a matter of definition with respect to the descriptions within this document, the lingual vestibules are bordered: superiorly by the ventral surface of the tongue, laterally by the mucosa covering the mandible, inferiorly by the floor of the mouth, and medially by the root of the tongue posteriorly. Anteromedially, at the midline of the mouth, the right and left lingual vestibules are continuous. Posteriorly the lingual vestibule is bordered by the oropharynx.

Referring to FIG. 1, one finds an illustration of the parts of the oral cavity (100) illustrated to aid one in understanding the descriptions given herein. Shown are the familiar parts of the mouth, specifically the lips (110), the teeth (120), and the tongue (130). The parts of the tongue (130) are the body of the tongue (131), the apex of the tongue (132), the dorsum of the tongue (133), the ventral of the tongue (134) and the deep lingual vasculature (137). One can clearly see that the body of the tongue (131) is rooted to the floor of the oral cavity by the lingual frenulum (140) between the sublingual papilla (150), in line with the apex of the tongue (132). Sublingual glands and a dense array of superficial vasculature (not illustrated) are covered by the sublingual mucosal covering (160).

Figure 2:
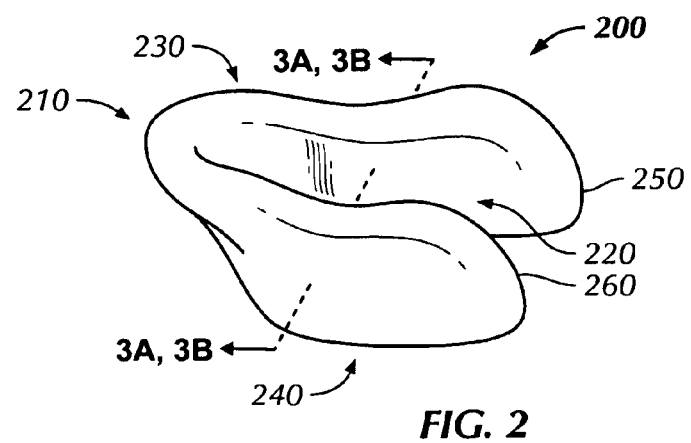
FIG. 2 illustrates a three-dimensional anatomic form of the bilateral lingual vestibular space in accordance with an exemplary embodiment of the invention.

FIG. 2 illustrates a three-dimensional anatomic form of the bilateral lingual vestibules in accordance with an exemplary embodiment of the invention. This three-dimensional anatomic mold of the lingular vestibular shape (200) has an anterior (210) and a posterior (220). The anatomical lingular vestibular mold's (200) shape is substantially mirrored along a midline plane which runs from the anterior (210) to the posterior (220) and extends from the superior (230) of the mold (200), which approximates the ventral surface of the tongue (134) to inferior (240), which approximates the floor of the mouth, where the sublingual mucosal covering (160) and sublingual papilla (150) are located. A left lingual vestibular flange (260) is shaped to occupy the space of the lingual vestibular region to the left of the lingual frenulum (140) and extending to the posterior of the oral cavity. A right lingual vestibular flange (250) is shaped to occupy the space of the lingual vestibular region to the right of the lingual frenulum (140) and extending to the posterior of the oral cavity. The left lingual vestibular flange (260) and the right lingual vestibular flange (250) are continuous at the midline on the anterior side (210) creating a void along the posterior (220). When the anatomical mold of the lingual vestibular shape (200) is placed in the oral cavity (100), the void will be occupied by the lingual frenulum (140) and the root of the tongue, and thus the mold will be held to the floor of the mouth by the body of the tongue (131), thus preventing slippage. Also illustrated is the location of the cross section (3A, 3B) from which FIGS. 3A and 3B were derived.

Figure 3A:
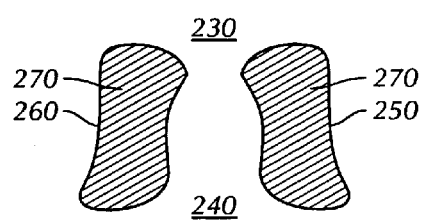
FIGS. 3A and 3B illustrate cross-sectional areas of a pharmaceutical dosage-form molded in a three-dimensional anatomic form of the bilateral lingual vestibules in accordance with an exemplary embodiment of the invention.

FIG. 3A illustrates a cross-sectional area of a bilateral lingual vestibular dosage-form molded in a three-dimensional anatomic form of the bilateral lingual vestibules in accordance with an exemplary embodiment of the invention. For reference, the superior/ventral tongue (230) and the inferior/floor of the mouth (240) are indicated. From the area shown, a cross section of the left lingual vestibular flange (260) is seen on the left of the figure, and a cross section of the right lingual vestibular flange (250) is seen on the right of the figure. The embodiment illustrated is constructed from a semi-permeable substrate structure (270), such as a mucoadhesive polymeric matrix, which is impregnated with a active substance/agent payload (not illustrated) which may be liquid, gaseous, or semi-solid in form. Such a payload would migrate from the supportive substrate (270) across the mucosal coverings into the vasculature and thus enter the patient's system.

Figure 3B:
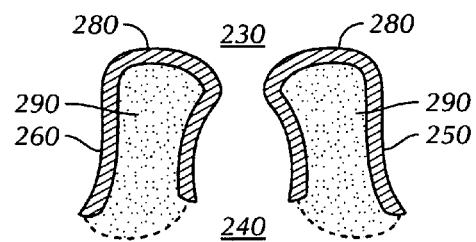

FIG. 3B illustrates a cross-sectional area of a hollow supportive substrate filled with a pharmaceutical payload and mucoadhesive polymer formed in a three-dimensional anatomic form of the lingual vestibular space in accordance with an exemplary embodiment of the invention. One skilled in the arts would appreciate that a pharmaceutical payload which possesses mucoadhesive properties may not require the addition of mucoadhesive polymer to serve the same purpose. For reference, the superior/ventral tongue (230) and the inferior/floor of the mouth (240) positions are indicated. From the area shown, a cross-section of the left lingual vestibular flange (260) is seen on the left of the figure, and a cross-section of the right lingual vestibular flange (250) is seen on the right of the figure. The embodiment illustrated is constructed from a hollow supportive substrate (280) which contains a pharmaceutical payload (290) which may be solid, or semi-solid in form. Such a payload would dissolve, melt, or in some other manner break-down or degrade to release at least the active pharmaceutical agents across the mucosal coverings into the vasculature and thus enter the patient's system. In this embodiment the bottom of the supportive substrate (280) is shown as open to the sublingual mucosal covering (160, not illustrated). In other embodiments the supportive substrate (280) may be more substantially closed with only minor openings to allow the pharmaceutical payload (290) to be released. In other embodiments the supportive substrate (280) may be open in other areas to direct the pharmaceutical payload to other parts of the oral cavity (110).

Figure 4A:
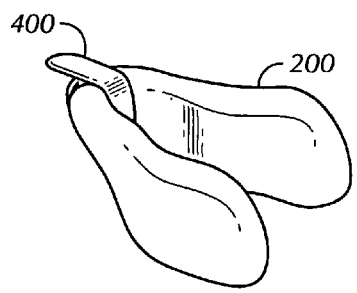
FIG. 4A through 4D illustrates handles and supportive substrates for use in bilateral lingual vestibular transmucosal pharmaceutical dosage-form and delivery systems in accordance with an exemplary embodiment of the invention.

FIG. 4A illustrates a handle attached to a three-dimensional anatomic form of the lingual vestibular space in accordance with an exemplary embodiment of the invention. The handle (400) is attached to a pharmaceutical delivery form which is an anatomic representation of the potential space formed by the bilateral lingual vestibules (200). In this embodiment, the handle is a flat tab-like structure which is affixed by a clip or band connected to the anterior joint between the left and right lingual vestibular flanges (260 and 250, not indicated)

Figure 4C:
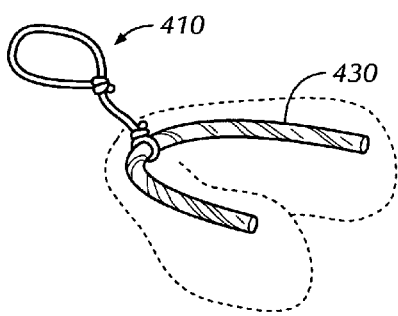
Figure 4B:
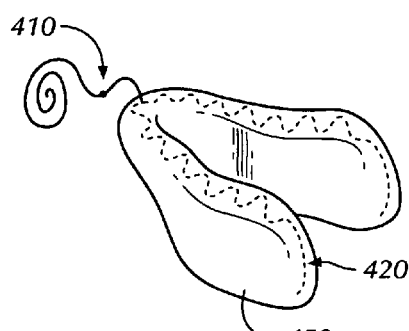

FIG. 4B illustrates a handle connected to an embedded supportive substrate in a three-dimensional anatomic form of the lingual vestibular space in accordance with an exemplary embodiment of the invention. The handle (410) is attached to a pharmaceutical delivery form which is an anatomic representation of the potential space formed by the bilateral lingual vestibules (200). In this embodiment the handle (410) is a string or band-like structure which is attached to more string or band like material (420) which is embedded in a moldable pharmaceutical payload (450). The pharmaceutical payload (450) illustrated is a three-dimensional shape formed to the potential space of the bilateral lingual vestibular shape. Other shapes could be used to produce other embodiments.

FIG. 4C illustrates a supportive substrate with attached handle for use in a lingual vestibular pharmaceutical delivery system in accordance with an exemplary embodiment of the invention. In the embodiment shown, a handle (410) is a string or band-like material which is attached to a U shaped flexible rod (430) which forms an internal structural support for the pharmaceutical delivery system. In the embodiment shown the U-shaped flexible rod is formed from a sheet material which has been gathered and twisted. The material from the handle (410) has been tied to the approximate middle of the rod (430). The two ends of the rod (430) are then bent such that the first end and the distal end are approximately parallel to one another.

Figure 4D:
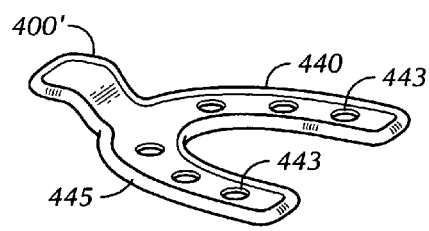

FIG. 4D illustrates a supportive substrate with attached handle for use in a lingual vestibular pharmaceutical delivery system in accordance with an exemplary embodiment of the invention. The molded supportive substrate (440) is formed from a substantially flat material formed into a "U" shape. The material may be further comprised of a surface texture which enhances the bonding of the pharmaceutical payload to the supportive substrate. The material has a plurality of openings (443) passing through the main body in several locations so that the formed pharmaceutical payload (290, not illustrated) can be attached above and below and joined through the openings to secure it to the supportive substrate (440). A rounded ridge, bead, or lip (445) is formed at the edge of the body. This helps to further secure the pharmaceutical payload (290, not illustrated) to the supportive substrate (440) and prevents sharp edges which may harm a patient's delicate oral tissue. A handle (400') is formed form the same material as the supportive substrate and is angled to be offset from the main body such that the main body may be situated in the lingual vestibule of a patient, and the handle may protrude from the oral cavity through the mouth. In the illustration, the handle is joined to the base of the "U" shape so that it would project directly from the front of the face. One skilled in the art would appreciate that such a handle could be of varying shapes and attached in varying ways to the main body. Further a handle could be angled to project from the side of the mouth at varying angles and still be in accordance with the teaching herein.

Figure 5A:
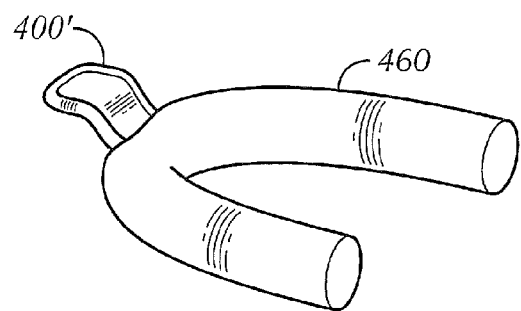
FIG. 5A through 5C illustrates embedded supportive substrates in molded bilateral lingual vestibular transmucosal pharmaceutical dosage-form and delivery systems in accordance with an exemplary embodiment of the invention.

FIG. 5A illustrates an embedded supportive substrate in a molded pharmaceutical payload system in a three-dimensional general form of the bilateral lingual vestibular space in accordance with an exemplary embodiment of the invention. Illustrated is a handle (400') attached to a supportive substrate (440, not visible) which is embedded in a moldable pharmaceutical payload (460). The pharmaceutical payload (460) in this embodiment has a general shape of a long cylinder which is curved near the middle into a general "U" shape to fit into the bilateral lingual vestibules.

Figure 5B:
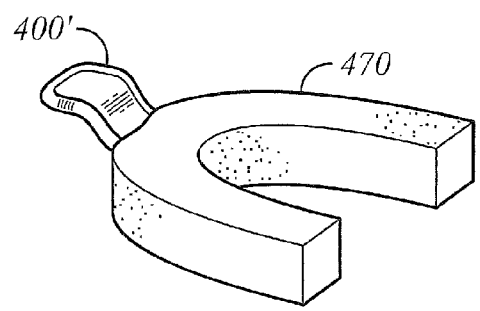

FIG. 5B illustrates an embedded supportive substrate in a molded pharmaceutical payload system in a three-dimensional general form of the bilateral lingual vestibules in accordance with an exemplary embodiment of the invention. Illustrated is a handle (400') attached to a supportive substrate (440, not visible) which is embedded in an anatomically moldable pharmaceutical payload (470). The pharmaceutical payload (470) in this embodiment has a semi- anatomical shape to fit into the bilateral lingual vestibules. One skilled in the art would appreciate that a perfect fit or custom mold, while an option, is not absolutely necessary due to the pliable nature of the oral tissue. Therefore several general sizes could be used to fit patients with different characteristics.

Figure 5C:
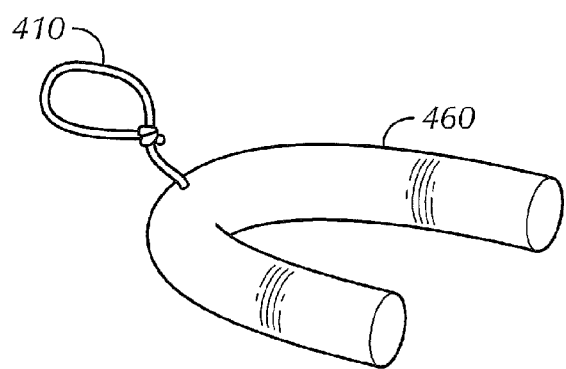

FIG. 5C illustrates an embedded supportive substrate in a molded pharmaceutical payload system in a three-dimensional general form of the lingual vestibular space in accordance with an exemplary embodiment of the invention. Illustrated is a handle (410) formed from a string or band type material and attached to a supportive substrate (430, not visible) which is embedded in a moldable pharmaceutical payload (460). The pharmaceutical payload (460) in this embodiment has a general shape of a long cylinder which is curved near the middle into a general "U" shape to fit into the lingual vestibule. One skilled in the art would appreciate that other shapes for the cross-sectional areas of the pharmaceutical payload (460) could be used in accordance with the teachings herein.

The diagrams in accordance with exemplary embodiments of the present invention are provided as examples and should not be construed to limit other embodiments within the scope of the invention. For instance, heights, widths, and thicknesses may not be to scale and should not be construed to limit the invention to the particular proportions illustrated. Additionally some elements illustrated in the singularity may actually be implemented in a plurality. Further, some element illustrated in the plurality could actually vary in count. Further, some elements illustrated in one form could actually vary in detail. Further yet, specific numerical data values (such as specific quantities, numbers, categories, etc.) or other specific information should be interpreted as illustrative for discussing exemplary embodiments. Such specific information is not provided to limit the invention.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A lingual vestibular transmucosal pharmaceutical delivery system comprising:
   a pharmaceutical dosage-form; and
   a pharmaceutical payload, wherein the pharmaceutical dosage-form comprises the pharmaceutical payload;
   wherein the pharmaceutical dosage-form comprises bilateral flanges connected at the anterior midline, wherein the flanges are shaped to coincide with anatomic tissue curvatures of the lingual vestibule so as to contact mucosal tissues bordering the lingual vestibule, whereby the pharmaceutical payload is transmucosally delivered via the mucosal tissues bordering the lingual vestibule, and wherein the pharmaceutical payload is 5-10 grams.

2. The transmucosal pharmaceutical delivery system of claim 1, wherein the bilateral flanges are connected at the anterior midline to form a "U" shape.

3. The transmucosal pharmaceutical delivery system of claim 1, wherein the pharmaceutical dosage-form comprises a supportive substrate.

4. The transmucosal pharmaceutical delivery system of claim 3, wherein the supportive substrate is semi-permeable and impregnated with the pharmaceutical payload.

5. The transmucosal pharmaceutical delivery system of claim 3, wherein the supportive substrate is a hollow shell filled with the pharmaceutical payload and is partially permeable to allow the transmucosal delivery of the pharmaceutical payload via the mucosal tissues bordering the lingual vestibule.

6. The transmucosal pharmaceutical delivery system of claim 1 further comprising a handle attached to the pharmaceutical dosage-form.

7. The transmucosal pharmaceutical delivery system of claim 3, wherein the pharmaceutical dosage-form contains the supportive substrate interiorly.

8. The transmucosal pharmaceutical delivery system of claim 7 further comprising a handle either attached to the supportive substrate or integral with the supportive substrate.

9. The transmucosal pharmaceutical delivery system of claim 3, wherein the supportive substrate is a semi-rigid structure.

10. The transmucosal pharmaceutical delivery system of claim 1, wherein the pharmaceutical dosage-form further comprises one or more mucoadhesive compounds.

11. The transmucosal pharmaceutical delivery system of claim 1, wherein the pharmaceutical dosage-form further comprises one or more retentive compounds.

12. The transmucosal pharmaceutical delivery system of claim 1, wherein the pharmaceutical dosage-form further comprises one or more permeation enhancers.

13. The transmucosal pharmaceutical delivery system of claim 1, wherein the supportive substrate comprises one or more mucoadhesive compounds and/or permeation enhancers.

14. The transmucosal pharmaceutical delivery system of claim 1, wherein the pharmaceutical payload further comprises one or more of the following: glucose, dextrose, sucrose, terbutaline, alanine, naloxone, arginine, and/or thiamine.

15. The transmucosal pharmaceutical delivery system of claim 6, wherein the handle is joined at the middle of the pharmaceutical dosage-form and angled away from the ends of the pharmaceutical dosage-form such that the handle projects outside of the oral cavity when the pharmaceutical dosage-form is inserted into the lingual vestibule.

16. The transmucosal pharmaceutical delivery system of claim 8, wherein the handle is joined at the middle of the supportive substrate and angled away from the ends of the supportive substrate such that the handle projects outside of the oral cavity when the pharmaceutical dosage-form is inserted into the lingual vestibule.

17. A lingual vestibular transmucosal pharmaceutical delivery system comprising:
   a pharmaceutical dosage-form; and
   a pharmaceutical payload, wherein the pharmaceutical dosage-form comprises the pharmaceutical payload;
   wherein the pharmaceutical dosage-form comprises bilateral flanges connected at the anterior midline, wherein the flanges are shaped to coincide with anatomic tissue curvatures of the lingual vestibule so as to contact mucosal tissues bordering the lingual vestibule, wherein each of the flanges comprises a bottom surface through which the pharmaceutical payload is transmucosally delivered via the mucosal tissues bordering the lingual vestibule, and wherein the bottom surface is non-planar.

18. The transmucosal pharmaceutical delivery system of claim 17, wherein the bottom surface comprises a curved surface.

19. A lingual vestibular transmucosal pharmaceutical delivery system comprising:
   a pharmaceutical dosage-form; and
   a pharmaceutical payload, wherein the pharmaceutical dosage-form comprises the pharmaceutical payload;
   wherein the pharmaceutical dosage-form comprises bilateral flanges connected at the anterior midline, wherein the flanges are shaped to coincide with anatomic tissue curvatures of the lingual vestibule so as to contact mucosal tissues bordering the lingual vestibule, wherein each of the flanges comprises an outer side surface through which the pharmaceutical payload is transmucosally delivered via the mucosal tissues bordering the lingual vestibule, and wherein the outer side surface is non-planar.

20. A lingual vestibular transmucosal pharmaceutical delivery system comprising:
   a pharmaceutical dosage-form; and
   a pharmaceutical payload, wherein the pharmaceutical dosage-form comprises the pharmaceutical payload;
   wherein the pharmaceutical dosage form bilateral flanges connected at the anterior midline, wherein the flanges are shaped to coincide with anatomic tissue curvatures of the lingual vestibule so as to contact mucosal tissues bordering the lingual vestibule, wherein each of the flanges comprises an inner side surface through which the pharmaceutical payload is transmucosally delivered via the mucosal tissues bordering the lingual vestibule, and wherein the inner side surface is non-planar.

21. A lingual vestibular transmucosal pharmaceutical delivery system comprising:
   pharmaceutical dosage-form; and
   a pharmaceutical payload, wherein the pharmaceutical dosage-form comprises the pharmaceutical payload:
   wherein the pharmaceutical dosage-form comprises bilateral flanges connected at the anterior midline, wherein the flanges are shaped to coincide with anatomic tissue curvatures of the lingual vestibule so as to contact mucosal tissues bordering the lingual vestibule, wherein each of the flanges comprises an upper surface through which the pharmaceutical payload is transmucosally delivered via the mucosal tissues bordering the lingual vestibule, and wherein the upper surface is non-planar.

22. The transmucosal pharmaceutical delivery system of claim 21, wherein the upper surface comprises a curved surface.

23. The transmucosal pharmaceutical delivery system of claim 1, wherein each of the flanges comprises an upper surface through which the pharmaceutical payload is transmucosally delivered via the mucosal tissues bordering the lingual vestibule.

24. The transmucosal pharmaceutical delivery system of claim 1, wherein each of the flanges comprises bottom, outer side, inner side, and upper surfaces through which the pharmaceutical payload is transmucosally delivered via the mucosal tissues of bordering the lingual vestibule.

25. A lingual vestibular transmucosal pharmaceutical delivery system comprising:
   a pharmaceutical dosage-form; and
   a pharmaceutical payload, wherein the pharmaceutical dosage form comprises the pharmaceutical payload;
   wherein the pharmaceutical dosage-form comprises bilateral flanges connected at the anterior midline, wherein the flanges are shaped to coincide with anatomic tissue curvatures of the lingual vestibule so as to contact mucosal tissues bordering the lingual vestibule, wherein each of the flanges comprises bottom, outer side, inner side, and upper surfaces through which the pharmaceutical payload is transmucosally delivered via the mucosal tissues bordering the lingual vestibule, and wherein each of the surfaces is non-planar.

26. The transmucosal pharmaceutical delivery system of claim 25, wherein each of the surfaces comprises a curved surface.

* * * * *